United States Patent
Vinogradov (10) Patent No.: US 7,573,261 B1
(45) Date of Patent: Aug. 11, 2009

(54) METHOD AND SYSTEM FOR THE GENERATION OF TORSIONAL GUIDED WAVES USING A FERROMAGNETIC STRIP SENSOR

(75) Inventor: Sergey A. Vinogradov, San Antonio, TX (US)

(73) Assignee: IHI Southwest Technologies, Inc., San Antonio, TX (US)

( * ) Notice: Subject to any disclaimer, the term of this patent is extended or adjusted under 35 U.S.C. 154(b) by 0 days.

(21) Appl. No.: 12/142,855

(22) Filed: Jun. 20, 2008

(51) Int. Cl.
*G01N 27/82* (2006.01)

(52) U.S. Cl. ........................... 324/240; 73/643

(58) Field of Classification Search ........ 324/209, 324/217, 219–221, 228, 238–240; 73/578, 73/579, 598, 600, 620, 643, 650
See application file for complete search history.

(56) References Cited

U.S. PATENT DOCUMENTS

| | | | |
|---|---|---|---|
| 4,497,209 A | 2/1985 | Kwun | |
| 4,711,120 A | 12/1987 | Kwun | |
| 4,979,125 A | 12/1990 | Kwun | |
| 5,180,969 A | 1/1993 | Kwun | |
| 5,456,113 A | 10/1995 | Kwun | |
| 5,457,994 A | 10/1995 | Kwun | |
| 5,581,037 A | 12/1996 | Kwun | |
| 5,747,696 A | 5/1998 | Kwun | |
| 5,767,766 A | 6/1998 | Kwun | |
| 5,821,430 A | 10/1998 | Kwun | |
| 5,970,434 A | 10/1999 | Kwun | |
| 6,000,288 A | 12/1999 | Kwun | |
| 6,134,947 A | 10/2000 | Kwun | |
| 6,201,391 B1 | 3/2001 | Kwun | |
| 6,205,859 B1 | 3/2001 | Kwun | |
| 6,212,944 B1 | 4/2001 | Kwun | |
| 6,294,912 B1 | 9/2001 | Kwun | |
| 6,295,677 B1 | 10/2001 | Kwun | |
| 6,373,245 B1 | 4/2002 | Kwun | |
| 6,396,262 B2 | 5/2002 | Kwun | |
| 6,404,189 B2 | 6/2002 | Kwun | |
| 6,424,150 B2 | 7/2002 | Kwun | |
| 6,429,650 B1 | 8/2002 | Kwun | |
| 6,624,628 B1 | 9/2003 | Kwun et al. | |
| 6,779,409 B1 | 8/2004 | Kwun | |

(Continued)

OTHER PUBLICATIONS

Piezoelectricity—Wikipedia, the free encyclopedia (9 pages) http://en.wikipedia.org/wiki/Piezoelectricity.

(Continued)

*Primary Examiner*—Bot LeDynh
(74) *Attorney, Agent, or Firm*—Ted D. Lee; Gunn, Lee & Cave, PC (57) ABSTRACT

A method is shown for magnetostrictive testing of structures using a magnetostrictive strip and magnetostrictive techniques. A torsional guided wave is generated in the magnetostrictive strip which is dry coupled or bonded to the structure. A magnetic field creates an induced bias along the longitudinal axis of the magnetostrictive strip, which magnetic field is sufficiently strong so that when an AC pulse applies an AC bias perpendicular to the induced bias, the AC bias does not override or saturate the induced bias. This allows for an increased signal to noise ratio in a reflected signal indicating a defect in the structure. The induce bias and the AC bias are created by respective windings around the magnetostrictive strip, which windings are perpendicular to each other.

12 Claims, 6 Drawing Sheets

U.S. PATENT DOCUMENTS

| | | |
|---|---|---|
| 6,815,948 B1 | 11/2004 | Kwun |
| 6,917,196 B2 | 7/2005 | Kwun |
| 6,925,881 B1 | 8/2005 | Kwun |
| 6,968,727 B2 | 11/2005 | Kwun |
| 7,019,520 B2 | 3/2006 | Kwun |
| 7,131,339 B2 | 11/2006 | Kwun |

OTHER PUBLICATIONS

SwRI wins R&D 100 Award for MsS Heat Exchanger Probe (2 pages), Southwest Research Institute (SwRI),2006,News Release, San Antonio, TX.

Magnetostrictive Materials (1 page), Aviation Research http://virtualskies.arc.nasa.gov/research/youDecide/magnetoStrictive.html.

Magnetic Domains—Wikipedia, the free encyclopedia (3 pages) http://en.wikipedia.org/wiki/Magnetic_domain.

Magnetostriction—Wikipedia, the free encyclopedia (2 pages) http://en.wikipedia.org/wiki/Magnetostriction.

Why does the transformer hum?, Magnetostriction, http://hyperphysics.phy-astr.gsu.edu/hbase/solids/magstrict.html.

Magnetostriction and Magnetostrictive Materials (2 pages), http://aml.seas.ucla.edu/research/areas/magnetostrictive/mag-composites/Magnetostriction.

Understanding Transformer Noise (6 pages), Federal Pacific.

Cheong, et al, Comparison of an Array of EMATs Technique and a Magnetostrictive Sensor Technique for a Guided Wave Inspection of a Pipe (4 pages),http://www.scientific.net, 2006.

METHOD AND SYSTEM FOR THE GENERATION OF TORSIONAL GUIDED WAVES USING A FERROMAGNETIC STRIP SENSOR

1. BACKGROUND OF THE INVENTION

This invention relates to a method and apparatus for the generation of torsional guided waves in a ferromagnetic strip sensor, more particularly, where the bias magnetic field is not overwridden by the alternating magnetic field pulse.

This is an improvement over U.S. patent application Ser. No. 11/970,378 filed on Jan. 7, 2008 having the same inventor and assignee, which application is hereby incorporated by reference.

2. BRIEF DESCRIPTION OF THE PRIOR ART

As computer technology has advanced, so has the technology related to sensors. Sensors provide the input for the computers to use in signal processing. Just as computers are used in every aspect of our daily life, computers are also used in evaluating structures to determine if the structures are safe, or if the structures have defects that may impair their safety. One of the problems in evaluating structures using sensors and computers is that not all parts of the structure are available for inspection to determine defects. For example, a bridge may have cables or beams that are inaccessible. Another example may be a containment vessel at a nuclear power plant where major portions of the vessel are buried underground and inaccessible. A further example may be pipes buried underground that are inaccessible.

While many other methods of inspection of inaccessible structures has been developed, one method that is still being developed is the use of magnetostrictive sensor technology to locate defects in inaccessible structures. A good article giving the current state of the art of magnetostrictive sensor technology is "Overview of Magnetostrictive Sensor Technology," *Journal of Intelligent Material Systems and Structure*, Vol. 18, October 2007, by Frederick T. Calkins, Alison B. Flatau and Marclo J. Daampino. In a nutshell, magnetostrictive materials convert magnetic energy to mechanical energy and visa-versa. If a magnetostrictive material is magnetized, it strains in the direction of magnetization. If an external force produces a strain on the magnetostrictive material, the magnetic state of the magnetostrictive material will change.

A good explanation of the physical changes in the magnetostrictive material in response to rapid magnetization or demagnetization is contained in U.S. Pat. No. 6,917,196 to Kwun, et al, more particularly, the explanation in conjunction with FIGS. 13A through 13C contained therein. Examples of good magnetostrictive materials are as follows:

Cobalt
Iron
Nickel
Ferrite
Terfenol-D
Metglass

Magnetostrictive materials were actually discovered in the 1840's by James Prescott Joule when he noticed that iron changed length in responses to changes in magnetism and named the phenomena the Joule effect. What occurs is the magnetic domains within the material align with the magnetic field causing the expansion. Similarly, when a magnetostrictive material is strained (stretched or compressed), its magnetic energy changes. This is the opposite of magnetostrictive action and the phenomena is called the Villari effect.

Some of the advantages of using a sensor made of magnetostrictive materials is the sensor can operate at higher temperatures than other types of sensors. Also the magnetostrictive materials can undergo higher strains with lower input voltages than other types of sensors.

Conventional magnetostrictive sensor techniques for generation of torsional guided waves use Wiedmann effect and require both permanent and alternating magnetic fields. The permanent and alternating magnetic fields may be applied directly to the specimen, or to a magnetostrictive strip with enhanced magnetostriction, which magnetostrictive strip is bonded or dry coupled to the specimen. The orientation of the permanent magnetic field determines the orientation of the permanent bias field, which in turn determines the initial orientation of the magnetic domains in the structure and/or strip.

The orientation of the alternating magnetic field is different from the permanent bias field. To elicit movement of the magnetic domain in the conventional manner, an AC current establishes a variable AC magnetic bias. The angle between the variable AC bias and the permanent magnetic field bias is 90°. This provides for magnetic domains to be aligned in such a direction that the torsional guided wave will be propagated in the direction perpendicular to the magnetic field bias. In the traditional way of generating a torsional guided wave, the orientation of the AC coil is coincident with the orientation of the magnetostrictive strip, and perpendicular to the direction of torisonal guided wave propagation.

The major disadvantage of the method described hereinabove is with establishing a permanent magnetic bias field where the magnetostrictive strip has significant length. In a majority of the cases, only residual magnetism of the magnetostrictive strip can be used for initial orientation of magnetic domains in the direction of the permanent magnetic field bias. Due to interference from the AC magnetic field with the residual magnetic fields, the strength of the residual fields tend to decrease, which reduces the signal-to-noise ratio of the whole system.

Another major disadvantage of the method described hereinabove is that the AC magnetic field overrides or saturates the permanent bias field. If the AC magnetic field overrides the permanent bias field, the full signal strength of the AC magnetic bias cannot be used in creating the AC magnetic field. To prevent the permanent bias field from being saturated and overridden, something in addition needs to be provided to maintain the permanent bias field. In the present invention, a DC voltage source is used to establish and maintain the permanent bias field to prevent it from being overridden by the AC magnetic bias. Also, an AC voltage source can be used if it has (1) a slower frequency from the AC magnetic bias, (2) a phase shift from the AC magnetic bias, or (3) been rectified.

OBJECTS OF THE INVENTION

It is an object of the present invention to provide a method and apparatus for the generation of torsional guided waves using a ferromagnetic strip sensor.

It is another object of the present invention to use magnetostrictive techniques that has a bias magnetic field of sufficient strength not to be overridden by an alternating magnetic field pulse when generating torsional guided waves.

It is another object of the present invention to generate torsional guided waves in a magnetostrictive strip that is bonded or dry coupled to a structure to create torsional guided waves in the structure.

It is yet anther object of the present invention to use a voltage to create a magnetic field bias in a magnetostrictive strip with the bias direction being along the longitudinal axis and, thereafter, to apply an alternating magnetic field pulse perpendicular to the magnetic field bias to create a torsional magnetic wave in the magnetostrictive strip.

It still another object of the present to use a single voltage source to create both a magnetic field bias along a longitudinal axis of a magnetostrictive strip and an alternating magnetic field pulse perpendicular thereto create a torsional guided wave in the magnetostrictive strip.

In the present invention, a magnetic field bias is created in a magnetostrictive strip by a voltage being applied to a coil wound around a short axis of the magnetostrictive strip. By applying a voltage to the short axis coil, a strong magnetic field bias is created.

In a second coil wound around the longitudinal axis of the magnetostrictive strip, a pulse of AC current is applied. This pulse of AC current generates an alternating magnetic field pulse in the magnetostrictive strip from the alternating current, which alternating magnetic field pulse is parallel to the short axis and perpendicular to the longitudinal axis. The applying of the alternating magnetic field pulse to the bias magnetic field generates a torsional guided wave within the magnetostrictive strip. The direction of propagation of the torsional guided wave is along the short axis of the magnetostrictive strip and perpendicular to the bias magnetic field.

The torsional guided wave is transferred from the magnetostrictive strip by either dry coupling or bonding to a structure under test. If there are defects in the structure, the torsional guided wave will be reflected off the defects. The reflected waves will be received by the magnetostrictive strip, sensed, and processed to determine size and location of the defects. The voltage being applied to generating the magnetic field bias is of sufficient strength to prevent the alternating magnetic field pulse from overriding the magnetic field bias.

While the magnetic field bias can be created by a DC voltage, the magnetic field bias can also be created by (1) a phase shifted alternating voltage, (2) a rectified AC voltage or (3) an AC voltage of a much slower frequency. In this manner, it is possible to use one power supply to provide both the magnetic field bias and the alternating magnetic field pulse.

One of the problems that has occurred in the past is that the alternating magnetic field pulse will override or saturate the magnetic field bias. If that is the case, then only a portion of the signal strength of the alternating magnetic field pulse, and hence the torsional guided wave, can be used. By providing a magnetic field bias that is not easily saturated or overridden, a much stronger strength signal can be obtained.

DETAILED DESCRIPTION OF THE PREFERRED EMBODIMENT

Figure 1:
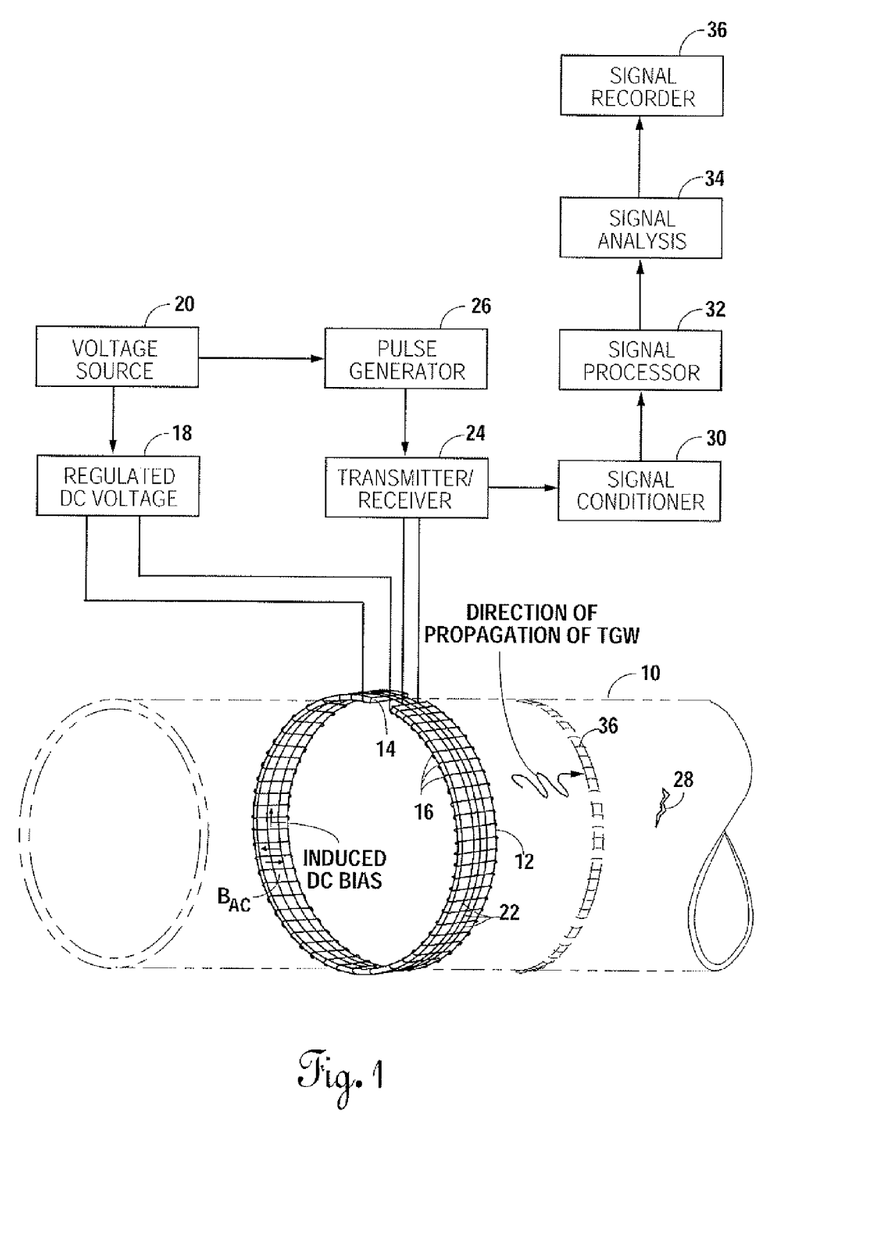
FIG. 1 is a system diagram of the present invention with a torsional guided waves being shown in pictorial view, which torsional guided waves are being generated in a magnetostrictive strip that is dry coupled or bonded to a pipe wherein the alternating magnetic field pulse will not override the magnetic field bias.

Referring now to FIG. 1 of the drawings, a pipe 10 is almost encircled by a magnetostrictive strip 12 except for a small gap 14 between the ends thereon. Wrapped around the short axis of the magnetostrictive strip 12 is a DC coil 16. The DC coil 16 receives a regulated DC voltage 18 from a voltage source 20.

Wrapped longitudinally around the magnetostrictive strip 12 is an AC coil 22. The AC coil 22 is connected to the transmitter/receiver 24. The transmitter/receiver 24 is connected to a pulse generator 26 that receives energy from the voltage source 20.

The magnetostrictive strip 12 may be pressed against the pipe 10 if the pipe 10 is ferromagnetic. Otherwise, if the pipe is not ferromagnetic, the magnetostrictive strip 12 may be bonded or dry coupled to the pipe 10.

In actual practice the voltage source 20 will supply power to a regulated DC voltage 18 which will then apply a DC voltage to the DC coil 16 wrapped around the short axis of the magnetostrictive strip 12. The DC voltage will create an induced DC bias in the direction indicated by the arrow on the magnetostrictive strip 12. After the induced DC bias is created in the magnetostrictive strip 12, a pulse generator 26 driven by the voltage source 20 will deliver an AC pulse through the transmitter/receiver 24 to the AC coil 22 wound around the longitudinal axis of the magnetostrictive strip 12. The AC pulse delivered to the AC coil 22 will create a $B_{AC}$ (an alternating bias) in the directions indicated by the arrows in FIG. 1. The pulse of alternating current being delivered to the AC coil 22 creates the $B_{AC}$, which causes a torsional guided wave in the magnetostrictive strip 12. Because of the bonding or the dry coupling of the magnetostrictive strip 12 to the pipe 10, the direction of propagation of the torsional guided wave is in the direction indicated by the arrow shown in pipe 10. If the pipe 10 is ferromagnetic, bonding or dry coupling may not be required.

If the torsional guided wave traveling along the pipe 10 hits a defect 28 in the pipe 10, the torsional guided wave that hits the defect 28 will be reflected back to the magnetostrictive strip 12. The reflected torsional guided wave from defect 28 is sensed in the magnetostrictive strip 12 by what is called the Villari Effect. The Villari Effect causes a voltage to be realized in the AC coil 22 and sensed by the transmitter/receiver 24. The sensed signal is sent to a signal conditioner 30. After feeding the sensed signal through the signal conditioner 30, a signal processor 32 processes the signal and the signal analysis 34 analyzes the signal. The final output is recorded in some type of signal recorder 36.

Figure 2:
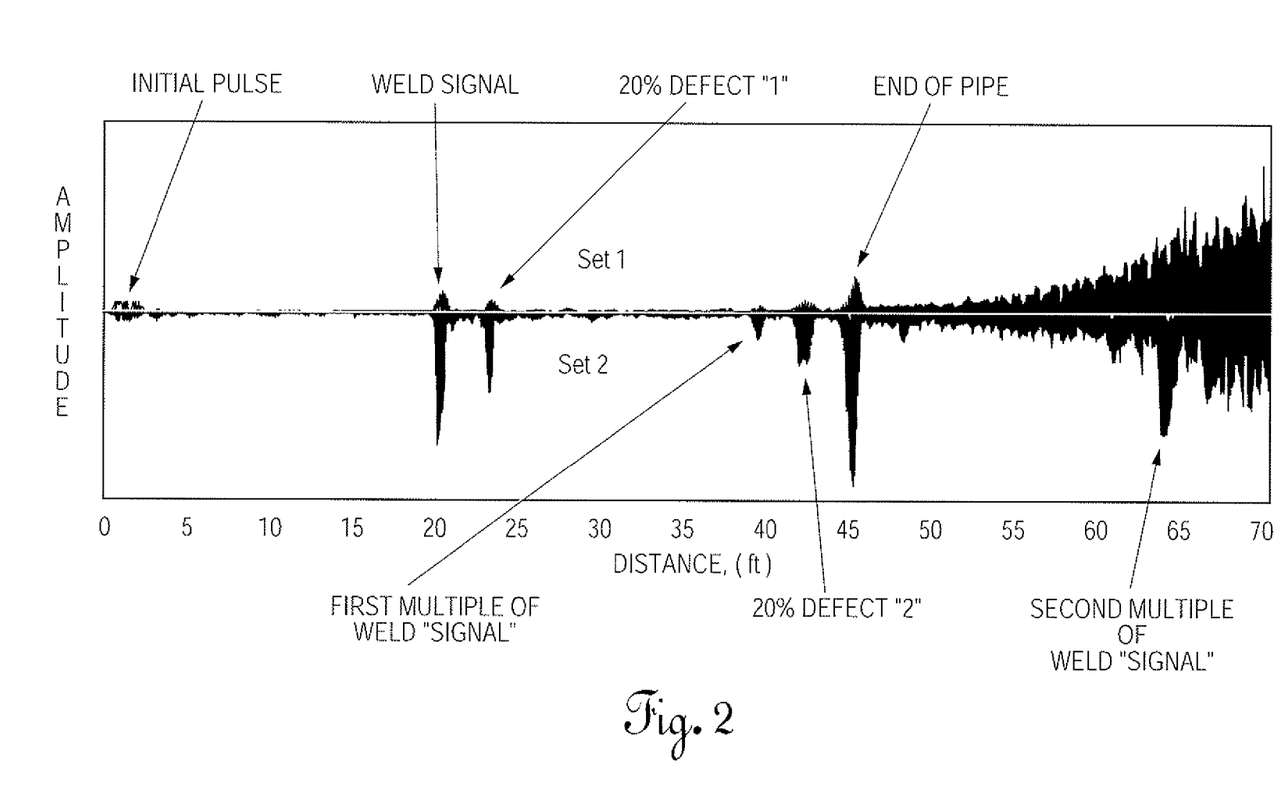
FIG. 2 shows two sets of data on the same pipe with Set 1 using traditional torsional guided waves and Set 2 using the present invention for an increased signal to noise ratio.

Referring to FIG. 2, two sets of data are illustrated. Set 2 at the bottom graph in FIG. 2 is the data that would be obtained using the system as shown in FIG. 1. A weld signal is shown as a result of welding two pipes together at weld 36 shown in FIG. 1. The 20% defect signal is the defect 28 in pipe 10. Other harmonics of the reflected signals may be received such as the first multiple of the weld signal or a harmonic of the defect signal. To get the type of signals as shown in Set 2, the regulated DC voltage 18 must continue to supply to the DC coil 16 a continuous induced DC bias. In other words, the pulse created by the pulse generator 26 that generates the alternating bias $B_{AC}$ cannot override or saturate the induced DC bias. This is prevented by providing a continually induced DC bias.

If a traditional method is used of creating the DC bias such as an elongated magnet, with all other things remaining the same, a set of data similar to Set 1 would be generated. As can be seen from the data, Set 1 to Set 2 is an eight to ten times stronger in signal strength. The reason for the stronger signal is because the regulated DC voltage 18 is continuously applied to the DC coil 16 which keeps an induced DC bias. This prevents the AC pulse from the pulse generator 26 through transmitter/receiver 24 that is delivered through the AC coil 22 and generates bias $B_{AC}$ from overriding or saturating the DC bias.

Figure 3:
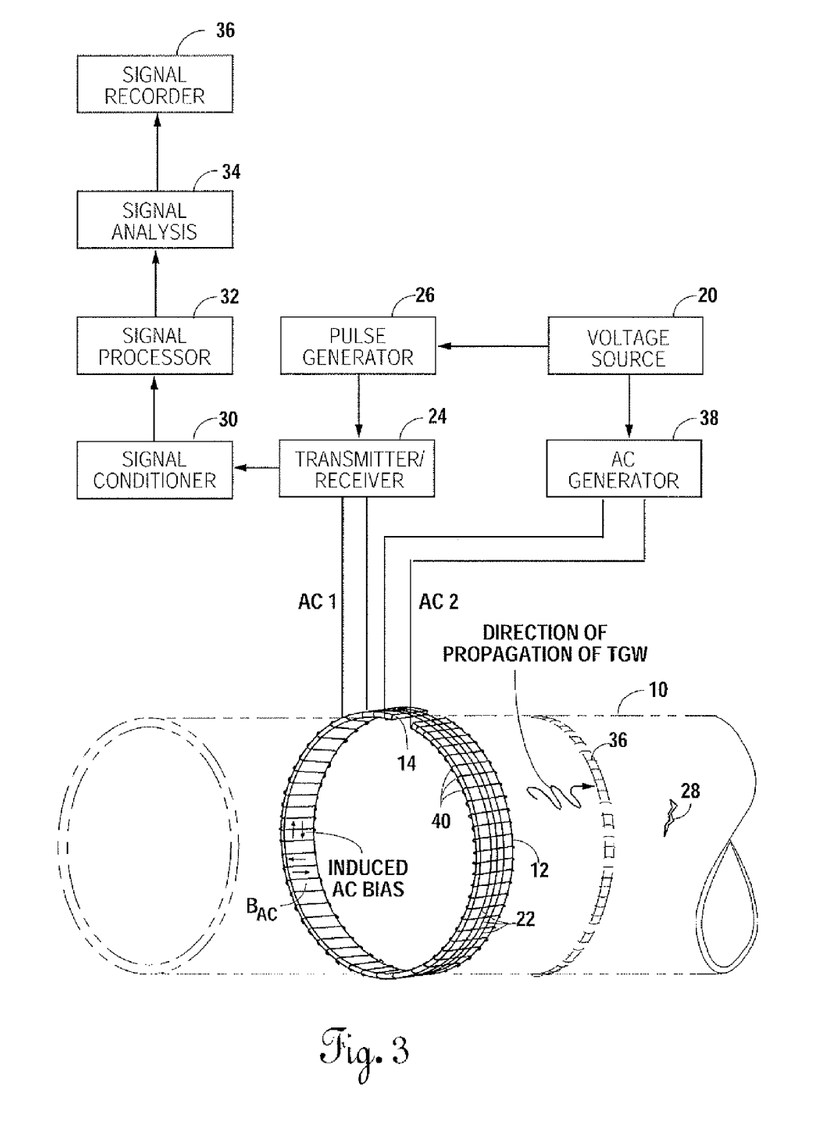
FIG. 3 is a system diagram of the present invention with torsional guided waves being shown in pictorial view, the magnetic field bias being generated by an AC generator.

In FIG. 3 an alternative embodiment of the present invention is shown. The pipe 10 with the weld 36 and defect 28 is again checked using a magnetostrictive strip 12. Again, a pulse generator 26 receives voltage from voltage source 20 to transmit a pulse through the transmitter/receiver 24 to the AC coil 40. However, rather than having a DC bias, as was explained in conjunction with FIG. 1, an AC generator 38 creates an induced AC bias as is indicated by the arrows. For an induced AC bias to work, it must be of a different frequency or phase shifted from the AC pulse generated by the pulse generator 26 and delivered via transmitter/receiver 24 to the AC coil 22.

Figure 5:
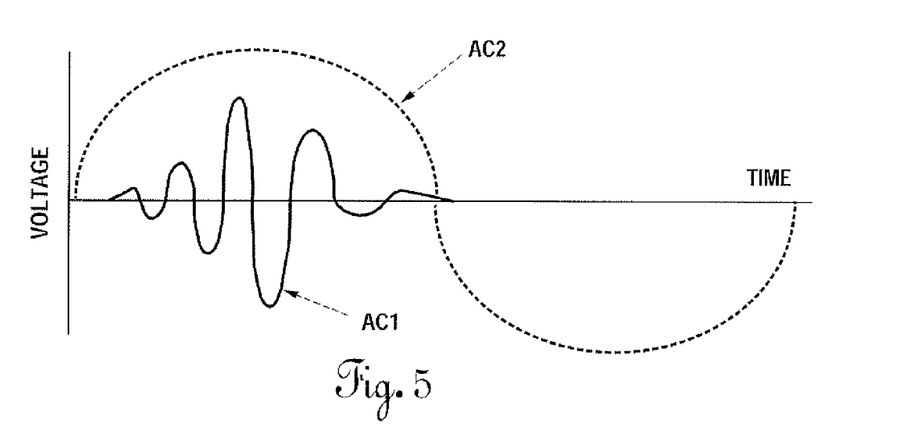
FIG. 5 is alternative example voltage wave forms that may be applied to the system shown in FIG. 3.

FIG. 5 shows one way the two AC voltages can be utilized, one from the AC generator 38 and another from the pulse generator 26. In FIG. 5 the AC pulse from the pulse generator 26 is indicated AC1. AC1 generates pulse bias $B_{AC}$ in the magnetostrictive strip 12. The induced AC bias from the AC generator 38 through the AC coil 40 is represented by the signal AC2 shown in FIG. 5. As can be seen in FIG. 5, a significant induced AC bias (AC2) is generated in the magnetostrictive strip at the time the pulse AC1 is delivered to AC coil 22. However, AC2 has a different frequency from AC1, Using the system as shown in FIG. 3, the voltage source 20 is turned on. AC generator 38 continuously generates the bias signal AC2 to create an induced AC bias through AC coil 40. Whenever a measurement is to be taken, pulse generator 26 generates a pulse signal AC1 which causes bias $B_{AC}$ in AC coil 22. This results in a torsional guided wave being released in the direction shown in FIG. 3. The torsional guided waves will reflect off of weld 36 or defect 28. The reflected signal will be received back at the magnetostrictive strip 12 and sensed in AC coil 22 by transmitter/receiver 24. Again, the reflected signal will be sent to a signal conditioner 30, signal processors 32 and signal analysis 34. The results of the signal analysis 34 can be read directly or sent to a signal recorder 36. The signal received would be similar to the signal received in Set 2 of the data of FIG. 2.

Figure 4:
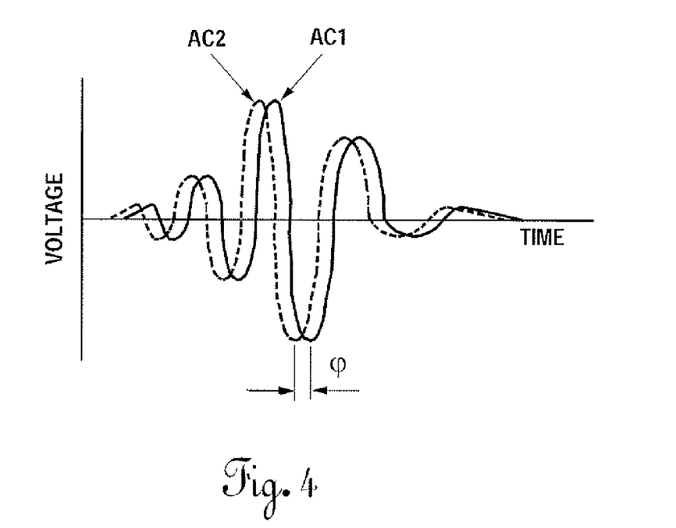
FIG. 4 is one example of wave forms that may be applied to the system shown in FIG. 3.

In another embodiment of the invention, the system as shown in FIG. 3 could generate a pulse signal AC1 as shown in FIG. 4. However, the signal generated by the AC generator 38 to be delivered to the AC coil 40 would be phase shifted 90° as shown by the signal AC2 of FIG. 4. In this manner, an induced AC bias would always be present at the time the pulse generates a bias $B_{AC}$ in the magnetostrictive strip 12.

Figure 6:
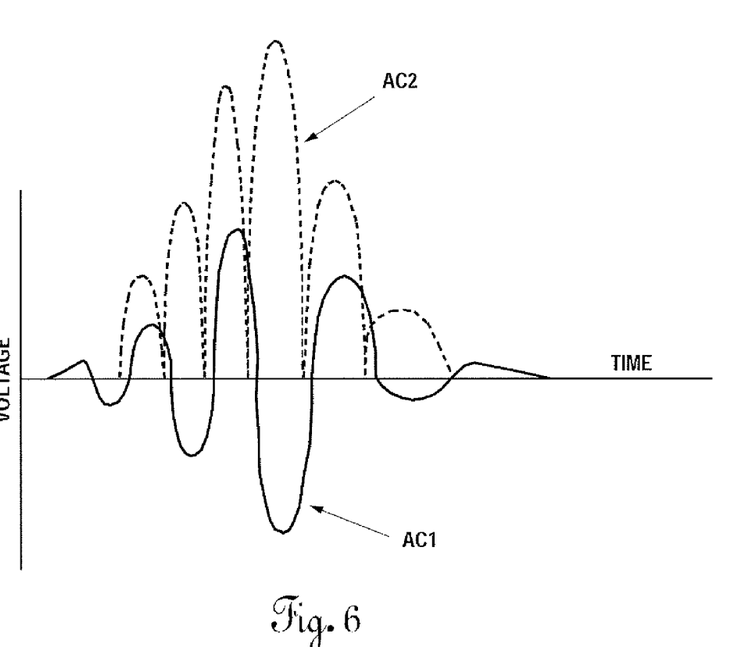
FIG. 6 is another alternative example voltage wave forms that may be applied to the system shown in FIG. 3.

A third type of wave form could be utilized in the embodiment shown in FIG. 3. The signal from the pulse generator 26 through the transmitter/receiver 24 delivered to the AC coil 22 could be AC1 as shown in FIG. 6. AC1 as shown in FIG. 6 is basically the same as AC1 shown in FIGS. 4 and 5. However, the signal being delivered by the AC generator 38 to the AC coil 40 would be AC2 as shown in FIG. 6. The signal AC2 as shown in FIG. 6 is essentially a rectified form of the signal AC1. By full wave rectification of the AC1 signal, the induced AC bias is generated in the magnetostrictive strip 12 through AC coil 40. Again, the wave forms as shown in FIG. 6 would work with the system as shown in FIG. 3.

Figure 7:
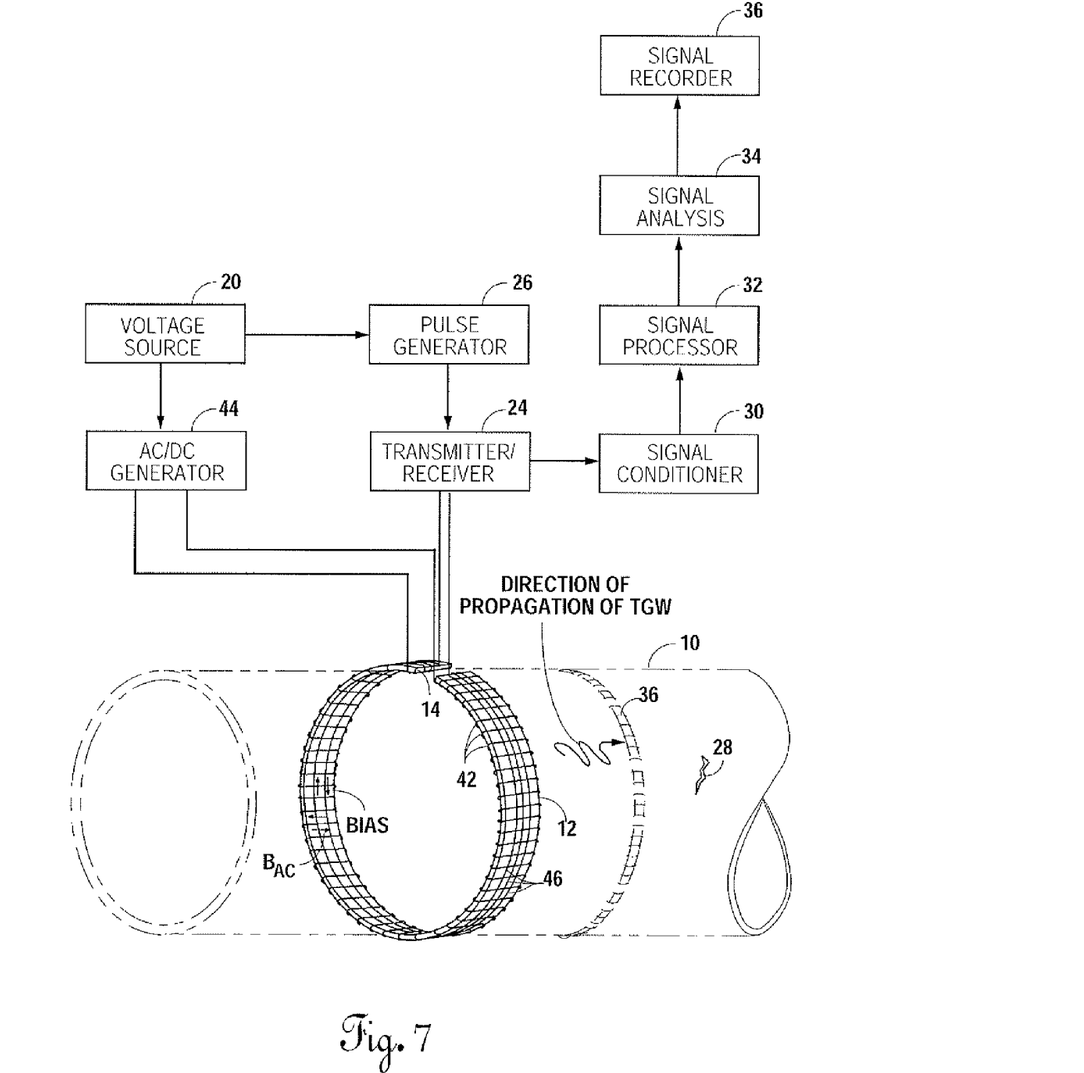
FIG. 7 is a system diagram of the present invention with the torsional guided waves being shown in pictorial form, the magnetic field bias being created by either an AC or DC voltage.

Referring to FIG. 7, a different configuration of the present invention is shown. The magnetostrictive strip 12 is the same with the small gap 14. Again, AC/DC coil 42 is wound about the short axis of the magnetostrictive strip 12. The voltage generator 20 through an AC/DC generator 44 will generate either an AC or DC bias in the magnetostrictive strip 12.

However, the AC coil 46 is wound around the longitudinal axis of the magnetostrictive strip 12 prior to it being applied to the pipe 10. Particularly note, the AC coil 46 is wound around the longitudinal axis in the magnetostrictive strip 12 prior to bending around pipe 10. Thereafter, the magnetostrictive strip 12 is bent in a circular manner to encircle pipe 10 with a small gap 14 between the ends thereof. The magnetostrictive strip 12 may be bounded or dry coupled to the pipe 10.

The pulse generator 26 will receive power from the voltage source 20. Whenever a measurement is to be taken, the pulse generator 26 will generate a pulse signal that is transmitted through transmitter/receiver 24 to the AC coil 46. This causes a torsional guided wave in the direction as indicated in FIG. 7. When a reflected signal is received off defect 28 or weld 36, the signal being received will be similar to Set 2 of the data shown in FIG. 2. The reflected signals from weld 36 or defect 28 are felt in the magnetostrictive strip 12 via AC coil 46. The signal in AC coil 46 is detected by transmitter/receiver 24 and conditioned in signal conditioner 30. From signal conditioner 30, the signal is processed by signal processor 32 and analyzed by signal analysis 34. Thereafter, the signal can be read directly or sent to signal recorder 36.

In the present invention, it is very important that the induced bias, whether it is AC or DC, not be overrun or saturated by the bias $B_{AC}$ generated by the pulse generator 26. By the providing of a continual induced bias signal, the saturation is prevented. Therefore, when a reflected signal is received back, there is an induced bias (whether AC or DC) present in the magnetostrictive strip so that the reflected signal can be sensed by the AC coil 22 or 46. By preventing the saturation of the induced bias, the reflected signal is eight to twelve times larger than it would otherwise be. The signal to noise ration is much greater which allows defects in a structure being monitored or tested to be determined much more readily.

I claim:

1. The method of nondestructive testing of a structure using magnetostrictive techniques to determine defects in the structure, said method comprising the following steps:

securing a magnetostrictive strip having a longitudinal axis and a short axis to said structure;

first applying a voltage to a short axis coil wound around said short axis to generate a bias magnetic field in said magnetostrictive strip, said bias magnetic field having a bias direction along a longitudinal axis of said magnetostrictive strip;

second applying a pulse of alternating current to an AC coil wound around said longitudinal axis of said magnetostrictive strip and in parallel to said bias magnetic field;

creating an alternating magnetic field pulse in said magnetostrictive strip from said pulse of alternating current, said alternating magnetic field pulse being parallel to said short axis;

generating a torsional guided wave in said magnetostrictive strip from said alternating magnetic field pulse, direction of propagation of said torsional guided wave being along said short axis and perpendicular to said bias magnetic field;

transferring said torsional guided wave from said magnetostrictive strip to said structure;

reflecting said torsional guided wave off said defects;

receiving said reflected torsional guided wave;

processing said received reflected torsional guided wave to determine size and/or location of said defects;

said voltage of said first applying step being sufficient to prevent said alternating magnetic field pulse from overriding said bias magnetic field.

2. The method of nondestructive testing of a structure using magnetostrictive techniques to determine defects in a structure as given in claim 1 further including after said processing step another step of recording said processed received reflected torsional guided wave.

3. The method of nondestructive testing of a structure using magnetostrictive techniques to determine defects in a structure as given in claim 2 wherein said magnetostrictive strip is dry coupled to said structure.

4. The method of nondestructive testing of a structure using magnetostrictive techniques to determine defects in a structure as given in claim 2 wherein said magnetostrictive strip is bonded to said structure.

5. The method of nondestructive testing of a structure using magnetostrictive techniques to determine defects in a structure as given in claim 2 wherein said voltage and said pulse of alternating current are received from a common source.

6. The method of nondestructive testing of a structure using magnetostrictive techniques to determine defects in a structure as given in claim 5 wherein said voltage is in alternating voltage.

7. The method of nondestructive testing of a structure using magnetostrictive techniques to determine defects in a structure as given in claim 6 wherein said alternating voltage is of a slower frequency than said alternating current.

8. The method of nondestructive testing of a structure using magnetostrictive techniques to determine defects in a structure as given in claim 6 wherein said alternating voltage is phase shifted by approximately 90° from said alternating current.

9. The method of nondestructive testing of a structure using magnetostrictive techniques to determine defects in a structure as given in claim 6 wherein said alternating voltage is rectified before generating said bias magnetic field.

10. The method of nondestructive testing of a structure using magnetostrictive techniques to determine defects in a structure as given in claim 1 wherein said structure is a pipe and said magnetostrictive strip is wrapped therearound with a gap between ends of said magnetostrictive strip.

11. The method of nondestructive testing of a structure using magnetostrictive techniques to determine defects in a structure as given in claim 10 wherein said AC coil is wound while said magnetostrictive strip is substantially flat so that said AC coil will be on both sides of said magnetostrictive strip when applied to said pipe.

12. The method of nondestructive testing of a structure using magnetostrictive techniques to determine defects in a structure as given in claim 10 wherein said AC coil is wound after said magnetostrictive strip is wrapped around said pipe so that said AC coil is only on an outside surface of said magnetostrictive strip.

\* \* \* \* \*